United States Patent [19]

Turley

[11] 4,154,239
[45] May 15, 1979

[54] DRUG PELLET IMPLANTER

[75] Inventor: Roger W. Turley, Hundon, Nr Sudbury, England

[73] Assignee: Hundon Forge Limited, Suffolk, England

[21] Appl. No.: 796,597

[22] Filed: May 13, 1977

[30] Foreign Application Priority Data

May 18, 1976 [GB] United Kingdom ............... 20377/76

[51] Int. Cl.² .............................................. A61M 5/00
[52] U.S. Cl. .................................................... 128/217
[58] Field of Search .................... 128/217, 215, 218 R, 128/218 D, 213

[56] References Cited

U.S. PATENT DOCUMENTS

| 2,883,984 | 4/1959 | Candido, Jr. et al. | 128/217 |
| 3,402,712 | 9/1968 | Eisenhand | 128/217 |
| 3,520,299 | 7/1970 | Lott et al. | 128/217 |
| 3,774,607 | 11/1973 | Schmitz | 128/217 |

FOREIGN PATENT DOCUMENTS 253175 7/1964 Australia .................................. 128/217

*Primary Examiner*—John D. Yasko
*Attorney, Agent, or Firm*—Oblon, Fisher, Spivak, McClelland & Maier

[57] ABSTRACT

An implanter by which pelleted drugs can be inserted or implanted under the skin of an animal typically to promote fattening of beef cattle and the like. The device includes a thurst pin which can be pushed through a tube containing the pellets to eject them into and through a hollow needle at the front of the device. A mechanism acts on the pin to push it in the forward direction and a return spring acts to return it to its rest position.

The mechanism includes a trigger lever as part of a handle assembly and movement is transmitted to the pin through a flexible link such as a cord or wire or belt or chain. The latter passes around abutments so as to reverse the direction of movement so that the pin is effectively pulled in the forward direction, the link being attached to a shuttle to which the rear of the pin is attached. A velocity ratio of for example 1:2 is employed so that the pin travels (in the case of that velocity ratio) twice the distance that the trigger lever travels thus enabling the device to be held and operated in one hand.

The tubes may be inserted one at a time in one embodiment. In other embodiments the tube-receiving region of the device is adapted to accept an array of tubes joined together to form a magazine typically in the form of a flat pack in which they are side by side or in the form of a cylinder.

12 Claims, 14 Drawing Figures

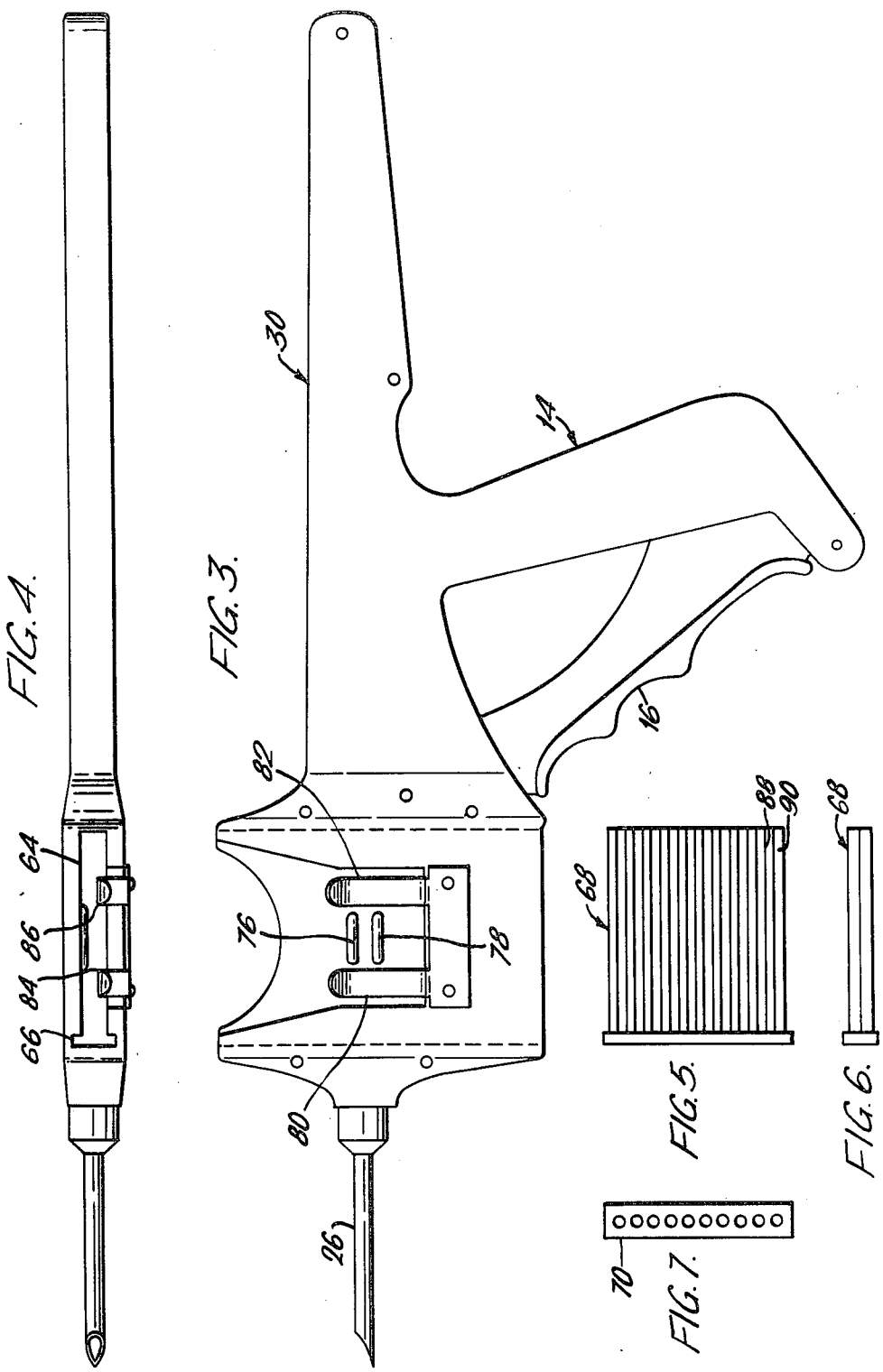

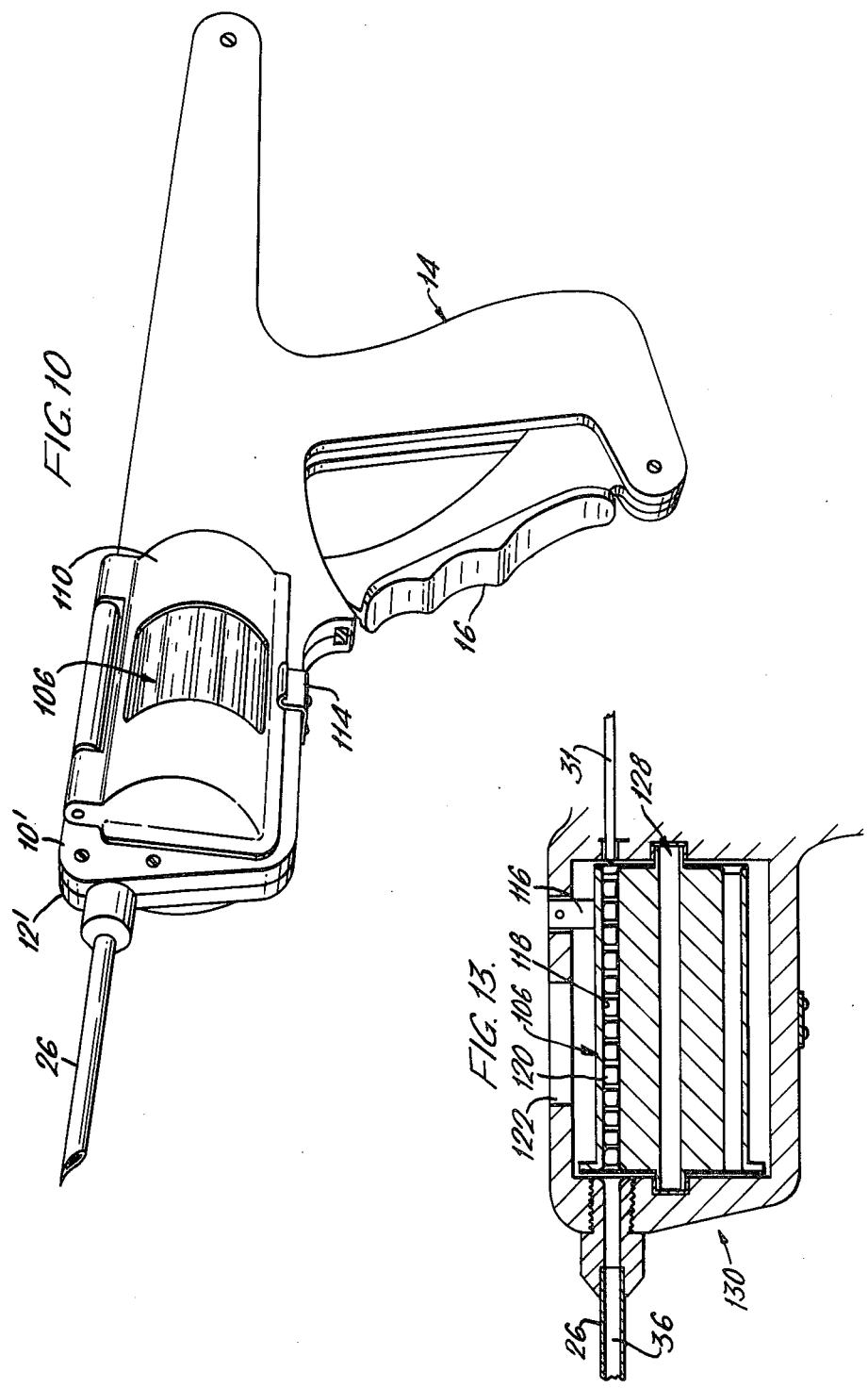

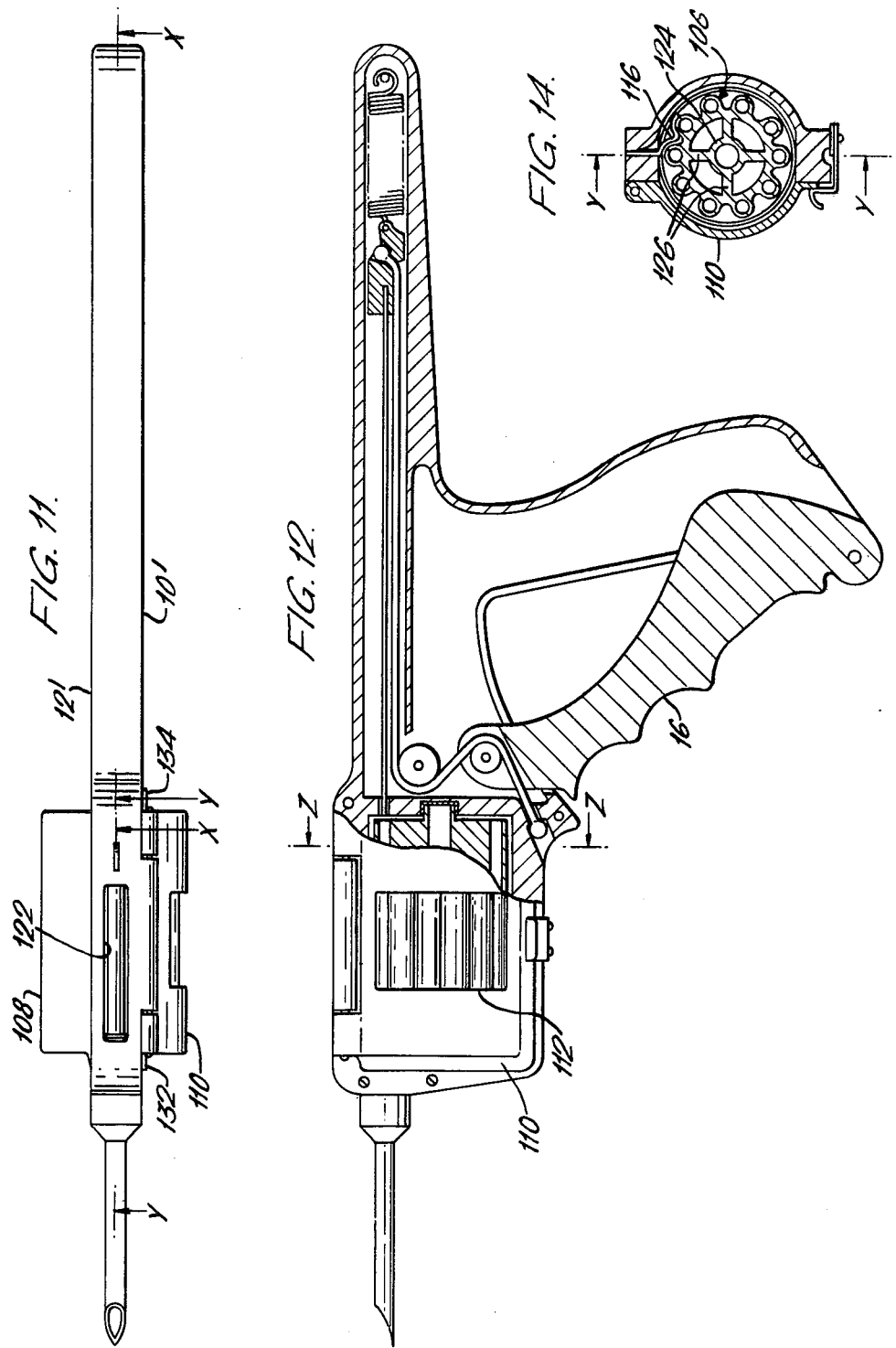

DRUG PELLET IMPLANTER

FIELD OF INVENTION

This invention concerns drug implanters for inserting pelleted drugs and the like below the skin of animals and livestock. The invention is of particular application in the livestock fattening industry in which growth promoting drugs have to be inserted below the skin of the animal. The pelleted drugs are commonly contained within a tube from which they have to be ejected.

DESCRIPTION OF THE PRIOR ART

A device for inserting pelleted drugs has been proposed in which a tube of pellets is located in alignment with a hypodermic type needle and a mechanism has been provided for pushing a pin through the aligned tube and needle so as to eject the pelleted drug from the tube into the hollow bore of the needle and finally out of the end of the needle under the skin of an animal into which the needle has been pushed to be absorbed by the animal in known manner.

Prior proposals have all included an actuator adapted to be pushed by the operator and a link between the actuator and the pin which acts in thrust to move the pin in a forward direction to push the pelleted drugs from the cylinder into the needle. The prior apparatus has suffered from the disadvantage that (i) buckling of the thrust link has occurred in practice, and (ii) the distance to be moved by the pin has determined the distance to be moved by the actuator and thrust link and invariably a 1:1 ratio has been employed in the prior proposals. With the tendency towards larger doses (i.e. a greater number of pellets to be inserted) apparatus in accordance with the prior proposals has required an excessive length of stroke i.e. distance to be moved by the actuator to produce implanting of the pellets, with consequent increase in the tendency for the even longer thrust link to buckle.

OBJECTS OF THE PRESENT INVENTION

It is one object of the present invention to provide an improved implanter which does not suffer from these two disadvantages.

It is another object to provide an implanter in which the distance to be moved by the actuator is less than the distance to be moved by the thrust pin for ejecting pelleted drugs from a tube.

It is another object to provide an implanter which is capable of receiving, and dispensing from, a magazine of tubes containing pelleted drugs.

SUMMARY OF THE INVENTION

According to the present invention an implanter for inserting pellets of a drug such as a drug for promoting growth, below the skin of a live animal comprises, a housing, a hollow needle having a sharpened end which protrudes from the housing and which can be inserted into the flesh of an animal so that the sharpened end is below the skin, a thrust pin which is movable in a forward direction into the rear of the hollow needle to force pellets therethrough, an actuator for moving the thrust pin in the said forward direction and a linkage between the actuator and the thrust pin which reverses the direction of movement of the actuator so that the latter is moved in a rearward direction to produce a forward movement of the pin.

By arranging that the actuator forms the trigger of a pistol grip, an implanter embodying the invention thus has the advantage that the complete device can be held and operated by one hand, leaving the other hand free to steady the animal and/or the implanter.

Preferably the linkage has a velocity ratio of less than unity so that the distance moved by the thrust pin is greater than the distance through which the actuator has to be moved to produce the movement of the thrust pin. Typically the velocity ratio is 1:2 (i.e. the distance moved by the thrust pin is twice the distance through which the actuator is moved).

Conveniently the linkage includes a flexible link in the form of a belt or chain or wire or cord which is preferably inextensible and one end of the flexible link being anchored to the housing and the other acting on the thrust pin, the link passing around a first abutment on the actuator and around a second abutment on the housing to achieve the reversal thrust and a velocity ratio of 1:2.

Alternatively for example the flexible link passes around a first abutment on the thrust pin and around a second abutment on the housing and is attached at its one end to the actuator and at its other end to a point on the housing in advance of the foremost position of the said first abutment when the thrust pin has been moved to its most forward position.

Where the actuator comprises the trigger of a pistol grip, it is preferably adapted so that it can be squeezed by the fingers of one hand to produce the required movement of the thrust pin.

Typically the pellets are contained in tubes (commonly referred to as capsules) which are introduced one tube at a time between the rear of the hollow needle and the forward end of the thrust pin when the latter is in a rest position. Conveniently a chamber is provided within the housing into which the tubes of pellets can be inserted, the housing being adapted to align the tube with the axis of the thrust pin and axis of the hollow needle to facilitate the entry of the thrust pin into the one end of the tube and the ejection of pellets from the other end of the tube into the hollow needle.

Typically the complete dose for an animal which comprises an appropriate number of pellets, is contained within a single tube. Thus a single implantation only is required per animal.

The chamber may be adapted to receive only one tube at a time and tubes may be introduced (and discarded after use) on a one at a time basis.

Alternatively the tubes may be joined to form a magazine and the chamber may be adapted to accommodate at least a part of the magazine which is movable relative to the housng so that successively, different tubes in the magazine can be located in line with the pin and needle.

The magazine may be in the form of a length of flat belt (similar to the cartridge belt employed with automatic repeat firing guns) or it may be in the form of an endless belt. The lateral connection between adjoining tubes in the magazine may be rigid or flexible.

There are two preferred forms of rigid array.

In a first preferred embodiment the tubes are rigidly joined in a side by side array to form a substantially flat package which can be pushed through the chamber tube by tube until spent.

In a second preferred embodiment the tubes are laterally joined in a rigid manner so as to form a cylindrical array in which the axis of the cylinder is parallel to the axes of the tubes which make up the array. The cylindrical array so formed preferably includes either a circular end plate at one or both ends or at least one or more internally formed spiders to provide support for central apertures or spigots for mounting the cylindrical array for rotation about the axis thereof to allow the array to be indexed one tube at a time relative to the thrust pin and needle so as to bring filled tubes successively into position between the thrust pin and needle.

Conveniently means may be provided to index the magazine by one tube after each operation of the actuator to eject pelleted drugs therefrom. In this way automatic operation of the implanter is achieved.

Preferably at least the pellets which will be ejected by the next stroke of the thrust pin are visible so that it is possible to see when all the tubes in the magazine are empty.

According to a further preferred feature of the invention, means is provided for locating the tube or tubes within the chamber, said means acting on one end of the tube or tubes only so that tubes of differing length can be fitted within the chamber (up to the maximum size permitted by the chamber).

Where a flat package magazine is employed, two laterally extending flanges may be provided at one end or the other of the array of tubes and the said means is adapted to act on the flanges so provided.

In the case of a cylindrical magazine, a circular flange may be provided at or near one end or the other of the tubes and the said means may be adapted to engage the annular lip formed by the circular flange protruding beyond the cylindrical array of tubes.

Preferably each tube includes a window or is formed from transparent or semi-transparent material typically a plastics material so that pellets located therewithin can be seen.

Preferably the tube or array of tubes forming a magazine is formed differently at one end from the other and the tube-receiving chamber is so formed that it is only possible to insert the tube or array of tubes into the chamber one way round.

Preferably means is provided for automatically returning the thrust pin to its rest position when the actuator is released. Typically the means for returning the thrust pin to its rest position comprises a spring acting either on the actuator or on the thrust pin or both.

BRIEF DESCRIPTION OF THE DRAWINGS

FIG. 3 is a side view of an implanter constructed as another embodiment of the invention, FIG. 4 is a plan view of the implanter shown in FIG. 3, from above, FIG. 5 is a side view of a flat package magazine for use with the implanter shown in FIGS. 3 and 4, FIG. 6 is a top plan view of the magazine of FIG. 5, FIG. 7 is an end view of the front end of the magazine of FIG. 5, FIG. 10 is a perspective view of a further implanter constructed as a third embodiment of the invention, FIG. 11 is a top plan view of the implanter shown in FIG. 10, FIG. 12 is a side view of the implanter shown in FIG. 11 cross-sectioned on the line X—X of FIG. 11, FIG. 13 is a side view of the front end of the implanter shown in FIG. 10 cross-sectioned on the line Y—Y of FIG. 11 and drawn to an enlarged scale, and FIG. 14 is a cross section through the front end of the implanter shown in FIG. 10 cross-sectioned on the line Z—Z of FIG. 12.

DESCRIPTION OF THE PREFERRED EMBODIMENTS

Figure 1:
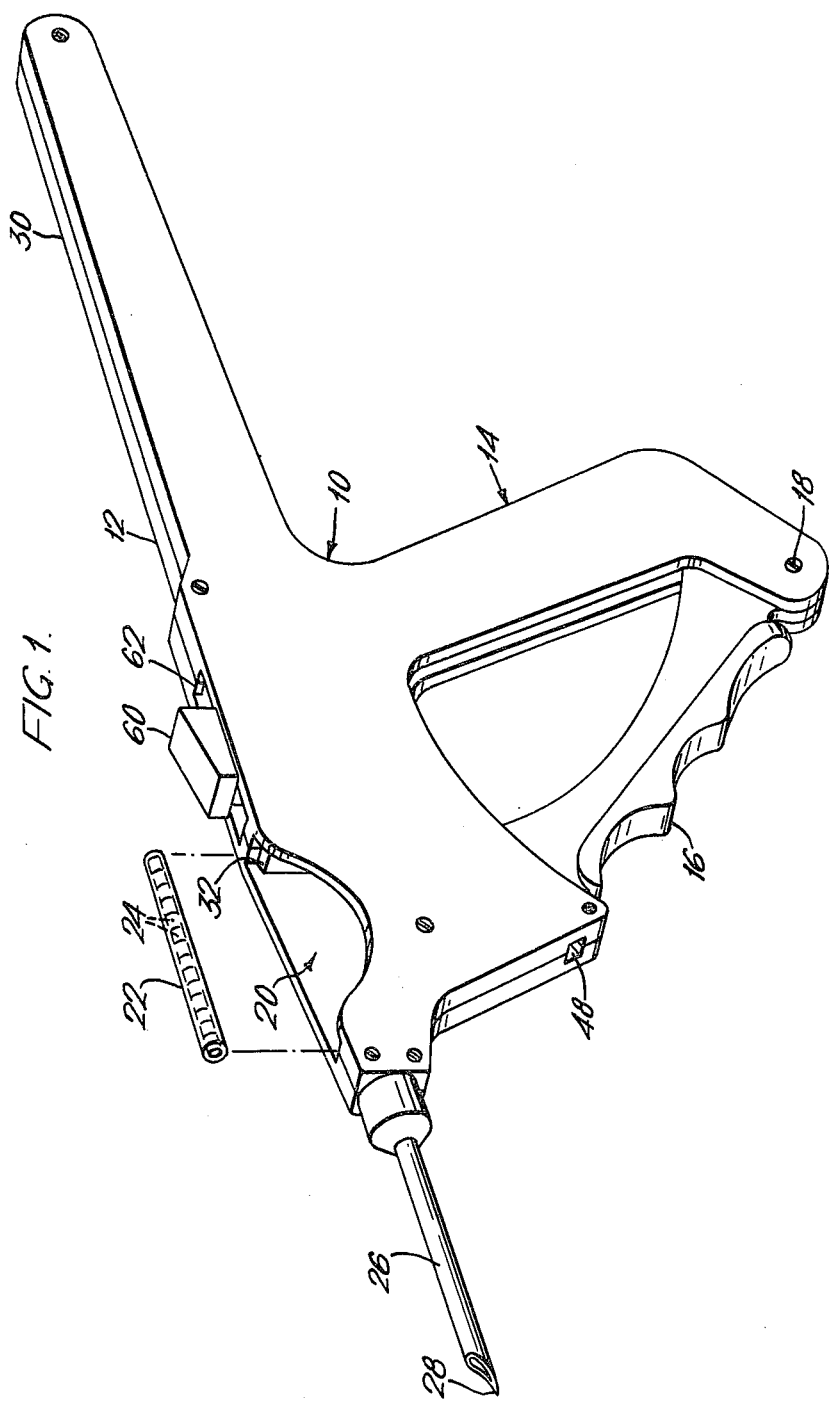
FIG. 1 is a perspective view of an improved implanter embodying certain aspects of the invention.
Figure 2:
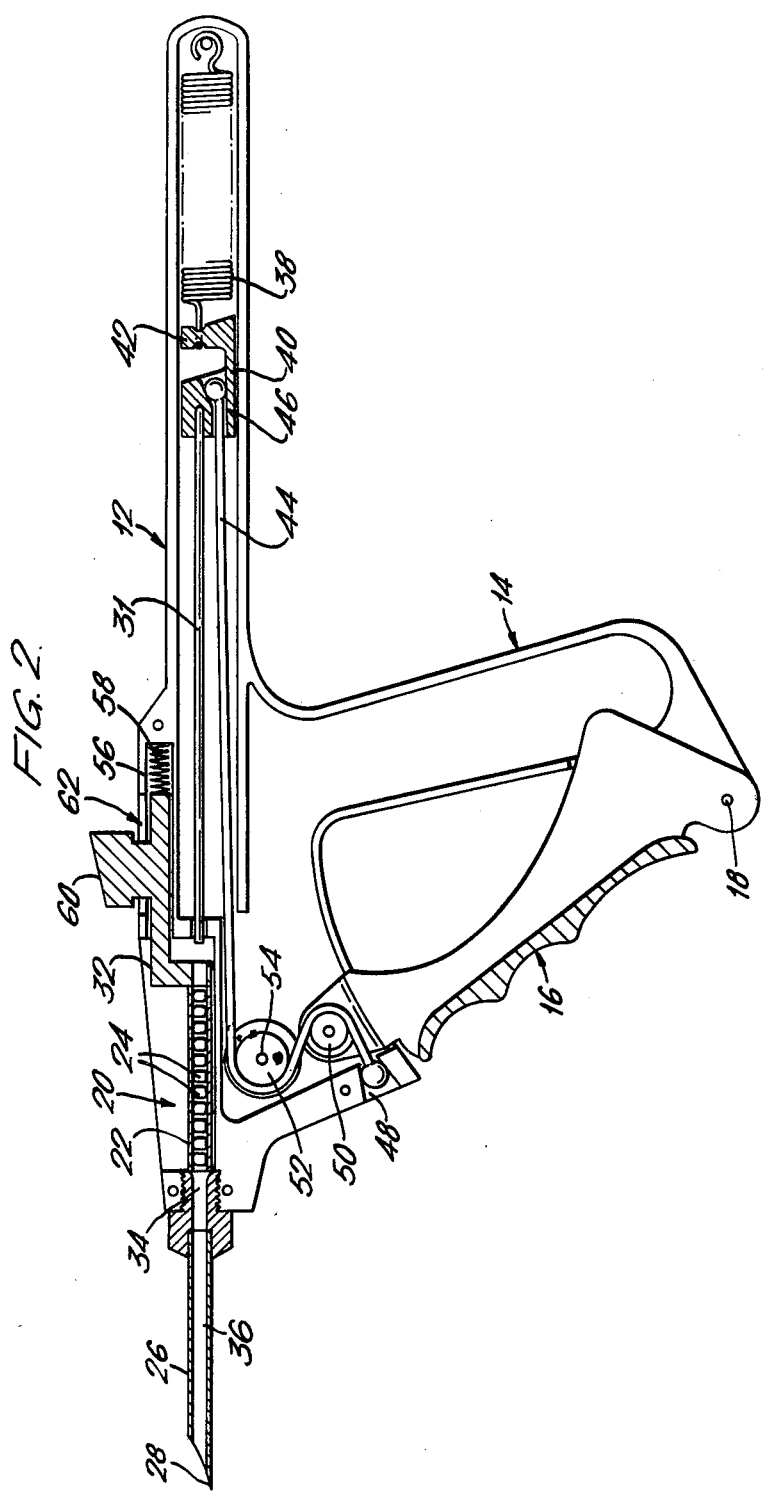
FIG. 2 is a side view of the implanter shown in FIG 1, shown in cross section to illustrate the mechanism by which movement is imparted to the thrust pin for ejecting drug pellets therefrom.

FIGS. 1 and 2 illustrate an implanter embodying the invention which comprises a housing for two parts 10 and 12 which are bolted together. The housing is generally T-shaped with the central stem of the T comprising a handle generally designated 14 the lower end of which is enlarged to form a step for housing a pivot joint for the lower end of a pistol grip lever 16. For convenience the pivot for the pistol grip lever 16 is provided around one of the securing screws 18 which serves to bolt the two parts 10 and 12 together.

The left hand section of the T includes a chamber generally designated 20 within which can be fitted a tube 22 containing pellets 24 of a drug which is to be used to promote fattening of cattle or the like.

At the forward end of the device there is situated a hollow needle 26 into which and through which the pellets are urged by a mechanism which will be described in more detail with reference to FIG. 2. By forcing the sharpened open end 28 of the needle under the skin of an animal (typically behind the ear lobe of the animal) the pellets can be inserted or implanted below the level of the skin from where the drug will be dispersed to promote the fattening of the animal.

The right hand section of the T denoted by reference numeral 30 comprises a housing within which is located the mechanism for pushing the pellets 24 out of the tube 22 and through the needle 26.

It will be seen from a study of the outside features of the implanter shown in FIG. 1 that the device is readily adapted to be used single-handed by an operator and leaves his other hand free so that he can either steady the implanter or the animal or both.

In FIG. 2 the cross section reveals the plunger pin 31 which is driven forward as the pistol grip lever 16 is squeezed in a rearward direction so as to pass first of all through an aligned aperture in a retaining clamp 32 (to be described in more detail hereinafter) and then through the hollow interior of a tube 22 located within the chamber 20 and finally through the aligned entrance passage 34 to enter the hollow interior 36 of the hollow needle 26. Forward movement of the pin 31 will thus result in displacement of a drug pellet form such as 24 in the tube 22 into and through the hollow needle 26 for implanting as previously described.

A return spring 38 is stretched as the pin 31 is moved in a forward direction and when the pistol grip lever 16 is released, the pin 31 is withdrawn to its rest position as the spring 38 relaxes.

The pin 31 extends from a shuttle 40 which runs in the interior of the housing extension 30. To this end the spring 38 is attached to an upstanding spigot 42 forming part of the shuttle 40.

Movement of the pistol grip lever 16 is imparted to the shuttle 40 through an inextensible flexible cord 44 which is anchored at one end in a tapering aperture 46 in the shuttle and at its other end in a tapering hole 48 in the housing just in advance of the upper end of the pistol grip lever 16. The cord 44 is formed with enlarged bulbous ends which cannot pass through the small ends of the respective tapering apertures 46 and 48 so that once in position, the cord remains under tension under the action of the spring 38. It will be seen however that for replacement and during initial assembly, insertion of a cord involves simply the forward movement of the shuttle 40 so as to allow the rear end of the cord to be released from the aperture 46 and having done that the slack cord can then be pulled rearwardly by a small amount from the aperture 48 and can then be slid sideways out of that aperture.

The cord 44 passes around a first pulley 50 carried at the upper end of the lever 16 and subsequently around a second pulley 52 mounted about a pivot 54 in the housing. After passing around the pulley 52, the cord extends directly to the shuttle 40. Rearward movement of the lever 16 will produce rearward movement of the pulley 50 and due to the velocity ratio of the arrangement, a movement of L along the arc of movement of the axis of the pulley 50 will produce a corresponding movement of approximately 2L of the shuttle 40 in the forward direction. Thus if a total stroke of 5" or thereabouts is required for the pin 31, a total movement of approximately 2½" only is required between the forward position of the lever 16 (as shown in FIG. 2) and its fully retracted position (not shown). It is this feature primarily which allows the device to be used with one hand since the 2½" movement of the lever 16 relative to the handle section 14 can be readily accommodated by the span of a man's hand.

Although the link 44 has been described as a cord it is to be understood that this may be replaced by a chain or by a belt or a wire or any other convenient flexible device.

The chamber 20 is adapted to receive tubes such as 22 of differing length by means of the spring-loaded clamp 32. This comprises an L-shaped member which is denoted by reference numeral 32 which is adapted to slide in a forward and backward direction in a passage 56 formed in the housing and which houses a spring 58 which is compressed when the L-shaped member 32 is slid backwards. To facilitate the rearward sliding of the member a button 60 protrudes through a slot 62 formed in the housing.

In operation, the button 60 is pushed as far back as possible and a tube 22 is inserted into the chamber 20. The button 60 is then released so that the L-shaped clamp member 32 springs forward under the action of a spring 58 so as to clamp the tube 22 in the chamber.

After the pellets 24 have been implanted from one tube, the spent tube can be removed from the housing by forcing back the button 60 against the spring 58 and shaking the implanter so that the spent tube falls out of the chamber which is then ready to receive the next full tube.

It will be appreciated that after each implantation, the implanter must be re-loaded with a fresh tube and this disadvantage of the embodiment shown in FIGS. 1 and 2 can be obviated by using either of the two remaining embodiments which will now be described.

FIGS. 3 and 4 illustrate an alternative implanter the internal mechanism of which is identical to the implanter shown in FIGS. 1 and 2 but which is modified so as to accommodate between the handle 14 and pistol grip lever 16 a rectangular section passage 64 which replaces the chamber 20 of the previous embodiment. At its front end the cross section of the passage 64 is enlarged at 66 and a magazine generally designated 68 and which includes ten tubes for retaining drug pellets and which is adapted to be used with the implanter shown in FIGS. 3 and 4, is shown in three views contained in FIGS. 5, 6 and 7. A magazine constructed on these lines is shown in more detail to an enlarged scale in FIG. 8 and a cross section through the magazine is shown in FIG. 9. The magazine is retained by means of a rectangular plate formation 70 which is located and formed integrally with the front of the tube assembly forming the magazine and the dimensions of this plate are such that it is just accommodated within the enlarged section 66 and the dimensions of the remainder of the magazine are such as to be accommodated within the remainder of the rectangular passage 64.

Figure 8:
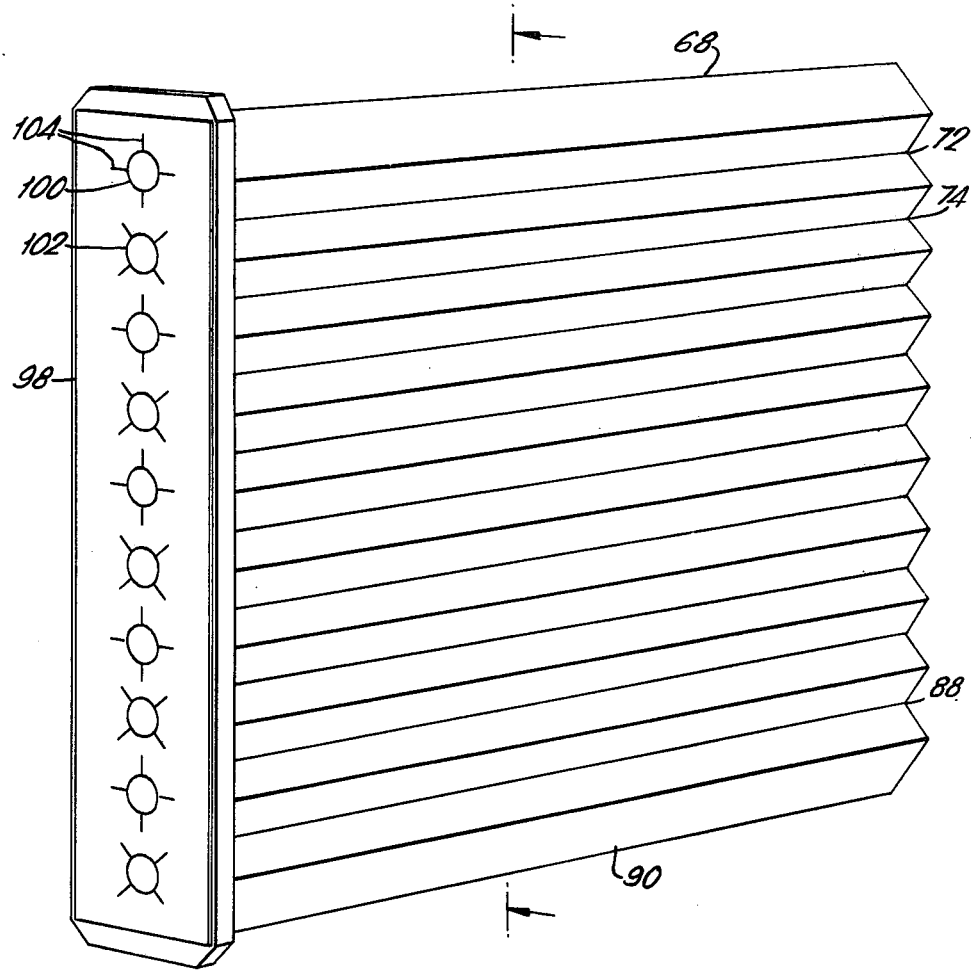
FIG. 8 is a perspective view to an enlarged scale of a preferred form of magazine similar to that shown in FIGS. 5 to 7.
Figure 9:
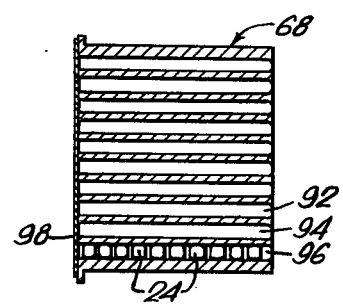
FIG. 9 is a cross-section view through the magazine shown in FIG. 8 (to a reduced scale)

The two sides of the magazine 68 include a series of parallel indentations 72, 74 etc. which are best seen in FIG. 8. These indentations are engaged by two complementary parallel abutments 76 and 78 formed approximately midway down one side wall of the passage 64 (see FIG. 3) and on the other side by two spring clips 80 and 82 which are formed with indentations 84 and 86 at their upper ends as shown in FIG. 4. The indentations 84 and 86 are aligned with the upper abutment 76 and the spring clips 80 and 82 extend into the passage 64 so that when a magazine 68 is pushed down into the passage 64, the two clips 80 and 82 are urged outwardly and the magazine is resiliently held in position and located by means of the engaging abutments 76 and 78 and the bent parts of the clips 80 and 82 formed by the indentations 84 and 86.

The two abutments 76 and 78 are located along the length of the passage 64 so that when the lowermost indentation 88 of the magazine is impaled on the one side by the abutment 76 and on the other side by the indentations 84 and 86, the lowermost tube 90 (see FIGS. 5 and 8) is aligned with the hollow needle 26 and (although not shown in FIG. 3) the pin 31.

In view of the location of the magazine 68 by the interaction between the flange 70 and the enlarged cross section 66, no additional locating means is required to accommodate cartridges of differing length. The only requisite is that the cartridge shall be long enough for part of the length to be engaged by at least part of the abutments 76 and 78 as the magazine is pushed through the passage 64.

FIGS. 8 and 9 demonstrate more clearly the detailed design of the magazine 68.

Each of the cylindrical bores 92, 94 etc. (shown in FIG. 9) is normally filled with a number of drug pellets 24 although for clarity only the lowermost bore 96 is shown as filled with pellets in the cross-section view of FIG. 9.

In order to facilitate filling of the magazine 68, each of the bores 92, 94, 96 etc. is formed with a reduced diameter opening at its right-hand end, the diameter of the opening being smaller than the diameter of the pellets 24 so as to prevent the pellets from passing therethrough and the other end (the left-hand end in FIGS. 8 and 9) of the bores is of sufficient diameter to allow the pellets to be introduced therethrough. The right-hand end of the bores 92, 94, 96 etc. are then closed by means of a strip of foil or like material 98 typically adhesivebacked foil having formed therein a plurality of holes 100, 102 etc. which align with the circular bores 92, 94, 96 etc. but are of smaller diameter than the diameter of the pellets 24 so that with the foil in position, the pellets are trapped within the bores. Small radial cuts such as 104 are formed around the holes 100, 102 etc. to facilitate the bursting open of the holes to allow the passage therethrough of the pellets under the action of the pin 31 as the latter is moved in a forward direction.

If it is desired that the pellets are sealed into the magazine against the ingress of moisture etc. a further layer of foil may be applied to opposite ends of the magazine so as to cover the openings at opposite ends of the bores 92, 94, 96 etc. Before the magazine is used, the foil overlying the foil layer 98 is removed and the magazine slipped into the passage 64.

An alternative embodiment of implanter is shown in FIGS. 10 to 14.

FIG. 10 is a perspective view of this alternative implanter which with regard to the operating mechanism is identical to that shown in FIGS. 1 and 2 but, as in the case of the embodiment shown in FIGS. 3 and 4, the forward end of the housing is modified and the chamber 20 is replaced by a chamber adapted to receive a cylindrical magazine generally designated 106 in FIG. 10. As shown in FIG. 1, the implanter is formed from a two-part housing 10' and 12' and referring to FIGS. 11 and 14, the housing section 12' is formed with a part cylindrical shell portion 108 in advance of the pistol grip lever 16. A complementary aperture is formed in the other housing part 10' which can be closed by a cover generally designated 110 also of part cylindrical form. When the cover 110 is in place (as shown in FIG. 10) a generally cylindrical chamber is formed within the housing into which a cylindrical magazine 106 can be fitted.

The cover 110 is cut away to form a window 112 through which the cylindrical magazine can be seen and which gives access to the external surface of the magazine to allow the latter to be indexed to permit different regions of the magazine to be aligned with the hollow needle 26.

A spring catch 114 retains the cover 110 in position and an index spring 116 (as shown in FIG. 14) engages the undulations of the external surface of the magazine 106. The undulations in the external surface of the magazine 106 lie between radial protrusions containing axial bores within which are located pellets. FIG. 13 which is cross section through the front end of the implanter shown in FIG. 10 illustrates the cylindrical magazine and shows one of the bores 118 filled with pellets 120 which is aligned with the axis of the pin 31 and the interior 36 of the hollow needle 26. It will be seen from FIG. 14 that by appropriate positioning of the radially directed indentation in the index spring 116, so one of the bores in the cylindrical magazine 106 will always be aligned with the pin 31 and hollow needle 26.

A refinement shown in FIG. 11 comprises a window 122 through which the upper bore in the cylindrical magazine can be seen. By providing an appropriate window in the wall of each bore or by forming the cylindrical magazine 106 at least in part from transparent or semi-transparent material, so it will be possible to see whether or not there is a charge of drug pellets ready to be implanted or whether the bore aligned with the needle is an empty one.

A further advantage of the index spring 116 is that it will readily permit the cylindrical magazine to be indexed in one direction (i.e. clockwise as shown in FIG. 14) but will not so readily allow indexing in the opposite anti-clockwise direction as shown in FIG. 14. In this way, by indexing the cylindrical magazine by one step in the same circular direction after each of the charges of drug pellets contained in each bore will be used in turn until the whole of the cylinder is spent.

As shown best in FIGS. 13 and 14, the cylindrical magazine 106 includes a hollow central core 124 which is joined to the interior of the cylindrical array of tubes by means of radial limbs 126 forming a so-called spider. The core 124 extends axially beyond the ends of the cylindrical array of tubes to form stub shafts 128 and 130 as shown in FIG. 13. The housing section 12' is cut away to form semi-circular recesses into which the stub shafts 128 and 130 fit and the cover 110 is formed with a lip 132 at one end and a lip 134 at the other end (see FIG. 11) which overlies the protruding semi-circular section of the stub shafts 128 and 130 and inhibits lateral movement of the cylindrical magazine 106.

It will be appreciated that provided the core section 124 remains the same, the axial length of the cylindrical array of tubes 106 is variable subject to a maximum dimension which will fit within the chamber. Thus shorter length cylindrical magazines (not shown) may be used accommodating smaller doses of pellets where required.

Although not shown in FIGS. 3 to 14, actuator means may be provided for indexing the magazine 68 or the cylindrical magazine 106 and the means may be independent of the pistol grip lever 16 or may be operated by each full squeeze of the lever 16 so that the magazine is indexed by one tube section for each operation of the implanter. In this event, means is also provided for indicating when all of the pellet-containing tubes have been emptied in a given magazine. Typically this may be in the form of a brightly coloured mark along the edge of the magazine (particularly the cylindrical magazine 106) which will become visible in the window 122 when the last batch of pellets from that magazine has been implanted.

I claim:

1. An implanter for inserting pellets of a drug below the skin a live animal comprising a housing, a hollow needle having a sharpened end which protrudes from the housing and which can be inserted into the flesh of an animal so that the sharpened end is below the skin, a thrust pin which is movable in a forward direction into the rear of the hollow needle to force pellets therethrough and an actuator adapted to be gripped and moved by an operator to produce a forward movement of the pin, a flexuose link between the actuator and the thrust pin which reverses the direction of movement of the actuator so that rearward movement of the latter produces a forward movement of the pin, the flexuose link being tensioned by movement of the actuator to transmit thrust to the pin wherein the flexuose link has a first end which is anchored to the housing and a second end which acts on the thrust pin, and a first abutment is provided on the actuator and a second abutment is provided in the housing around which the flexuose link passes to achieve the reversal of the thrust.

2. An implanter as set forth in claim 1 wherein the said flexuose linkage has a velocity ratio of less than unity so that the distance moved by the thrust pin is greater than the distance through which the actuator has to be moved to produce the said movement of the thrust pin.

3. An implanter as set forth in claim 2 wherein the velocity ratio is 1:2 so that the distance moved by the thrust pin is twice the distance through which the actuator is moved.

4. An implanter as set forth in claim 1 which further comprises a chamber within the housing into which tubes of pellets can be inserted, the housing being adapted to align the tube with the thrust pin and the hollow needle to facilitate the entry of the thrust pin into the one end of the tube and the ejection of pellets from the other end of the tube into the hollow needle.

5. An implanter as set forth in claim 4 wherein the tubes are joined to form a magazine and the chamber is adapted to accommodate the magazine in a plurality of different positions so that successively different tubes in the magazine can be located in line with the pin and needle.

6. An implanter as set forth in claim 5 in which the tubes are rigidly joined in a side by side array to form a substantially flat rigid package which can be pushed through the chamber tube by tube until spent.

7. An implanter as set forth in claim 5 in which the tubes are joined in a rigid manner so as to form a cylindrical array in which the axis of the cylinder is parallel to the axes of the tubes which make up the magazine.

8. An implanter as set forth in claim 5 which further comprises means for indexing the magazine by one tube after each operation of the actuator so as to present the next filled tube in the magazine to the thrust pin and needle.

9. An implanter as set forth in claim 1 further comprising means for locating one end of the tube in the chamber so that tubes of differing length can be accommodated within the chamber up to the maximum size permitted by the chamber.

10. An implanter as set forth in claim 1 further comprising means for automatically returning the thrust pin to its rest position when the actuator is released.

11. An implanter as set forth in claim 1 wherein the flexuose link is a wire.

12. An implanter for inserting pellets of a drug below the skin of a live animal comprising a housing, a hollow needle having a sharpened end which proturdes from the housing and which can be inserted into the flesh of an animal so that the sharpened end is below the skin, a thrust pin which is movable in a forward direction into the rear of the hollow needle to force pellets therethrough and an actuator adapted to be gripped and moved by an operator to produce forward movement of the pin, a flexuose link between the actuator and the thrust pin which reverses the direction of movement of the actuator so that rearward movement of the latter produces a forward movement of the pin, the flexuose link being tensioned by movement of the actuator to transmit thrust to the pin wherein the flexuose link has a first end which is attached to the actuator and a second end which is attached to a point on the housing, and a first abutment is provided on the thrust pin and a second abutment is provided in the housing around which the flexuose link passes, the position of the said point being in advance of the foremost position of said first abutment when the thrust pin has been moved to its most forward position.

* * * * *